United States Patent [19]

Umemura et al.

[11] 4,224,456
[45] Sep. 23, 1980

[54] PROCESS FOR PREPARING ALIPHATIC MONOCARBOXYLIC ACID ESTER OF HYDROXYMETHYL-SUBSTITUTED MONOAROMATIC COMPOUND

[75] Inventors: Sumio Umemura; Kanenobu Matsui; Kunitoshi Koga; Mineo Kuniyoshi, all of Ube, Japan

[73] Assignee: Ube Industries, Ltd., Yamaguchi, Japan

[21] Appl. No.: 908,732

[22] Filed: May 23, 1978

[30] Foreign Application Priority Data

May 30, 1977 [JP] Japan .................................. 52-62159

[51] Int. Cl.² ............................................. C07C 67/05
[52] U.S. Cl. ................................... 560/241; 252/430; 252/472; 252/473; 252/474
[58] Field of Search ................ 560/241; 252/430, 472, 252/473, 474

[56] References Cited

U.S. PATENT DOCUMENTS

| | | | |
|---|---|---|---|
| 3,547,982 | 12/1970 | McKeon et al. | 560/241 |
| 4,033,999 | 7/1977 | Onoda et al. | 560/241 |

*Primary Examiner*—Vivian Garner
*Attorney, Agent, or Firm*—Miller & Prestia

[57] ABSTRACT

Disclosed is a vapor phase catalytic oxidation process for preparing an aliphatic carboxylic acid ester of a monoaromatic compound having 1 to 2 hydroxymethyl substituents, such as benzyl acetate, p-methylbenzyl acetate, p-xylylenediacetate, benzyl propionate and benzyl butyrate. A gaseous feed comprised of a benzene compound having 1 to 2 methyl substituents, an aliphatic monocarboxylic acid having 2 to 4 carbon atoms and molecular oxygen is contacted with an improved catalyst. The metal ingredients of the catalyst consist essentially of (a) palladium, (b) arsenic and (c) at least one metal selected from alkali metals and alkali earth metals, and the atomic ratio of palladium:arsenic:the alkali or alkali earth metal is 1:0.05–4:0.1–10.

10 Claims, No Drawings

PROCESS FOR PREPARING ALIPHATIC MONOCARBOXYLIC ACID ESTER OF HYDROXYMETHYL-SUBSTITUTED MONOAROMATIC COMPOUND

This invention relates to a process for preparing an aliphatic carboxylic acid ester of a benzene compound having 1 to 2 hydroxymethyl substituents by the vapor phase catalytic oxidation reaction.

The aliphatic carboxylic acid esters of a benzene compound having 1 to 2 hydroxymethyl substituents to be prepared by the process of the invention include, for example, benzyl acetate, p-methylbenzyl acetate, p-xylylenediacetate, benzyl propionate and benzyl butyrate. These carboxylic acid esters are suitable for use as, for example, perfumes, colognes and paint solvents.

It is well known, as disclosed in Japanese Patent Publication No. 13081/67, that palladium exhibits a catalyst activity for the preparation of an aliphatic carboxylic acid ester of a benzene compound having one or more hydroxymethyl substituents, by reacting toluene or xylene together with a lower aliphatic monocarboxylic acid and with molecular oxygen. However, a catalyst consisting of palladium is not satisfactory in terms of both catalytic activity and durability thereof. Furthermore, palladium is expensive. Thus, it has been heretofore eagerly desired to develop improved palladium catalysts exhibiting an enhanced yield of and selectivity for the intended carboxylic acid ester proportional to the amount of palladium used.

For the above-mentioned purpose, some improved palladium catalysts have been proposed. For example, Japanese Patent Publication No. 28947/75 discloses a palladium catalyst combined with co-catalytic ingredients of bismuth, cobalt and iron. Furthermore, Japanese Patent Laid-open Application No. 108232/75 discloses a palladium catalyst combined with co-catalytic ingredients of antimony and an alkali or alkali earth metal. These proposed palladium catalysts exhibit enhanced catalytic activity and durability as compared with the catalyst comprised solely of palladium.

An object of the present invention is to provide a process for preparing an aliphatic carboxylic acid ester of a benzene compound having 1 to 2 hydroxymethyl substituents from a benzene compound selected from the group consisting of toluene and xylene, and an aliphatic monocarboxylic acid having 2 to 4 carbon atoms by using an improved palladium catalyst which exhibits more enhanced catalytic activity and durability and which provides a more enhanced yield of and selectivity for the intended compound, as compared with known palladium catalysts.

In accordance with the present invention, there is provided a process for preparing an aliphatic carboxylic acid ester of a benzene compound having 1 to 2 hydroxymethyl substituents bound to the nucleus, which comprises the step of contacting, in a vapor phase, a gaseous feed comprised of a benzene compound selected from the group consisting of toluene and o-, m- and p-xylenes, an aliphatic monocarboxylic acid having 2 to 4 carbon atoms and molecular oxygen with a catalyst, wherein the metal ingredients of the catalyst consist essentially of (a) palladium, (b) arsenic and (c) at least one metal selected from the group consisting of alkali metals and alkali earth metals, the atomic ratio of palladium:arsenic: the alkali or alkali earth metal being 1:0.05–4:0.1–10.

The benzene compound used as a starting material in the process of the invention includes toluene and o-, m- and p-xylenes. The aliphatic monocarboxylic acid also used as a starting material includes acetic acid, propionic acid and butyric acid. It is advantageous from the standpoint of space time yield of and selectivity for the intended product that the proportional amounts of these two starting materials in the gaseous feed be such that the amount of the aliphatic monocarboxylic acid is larger than the stoichiometric amount. In general, the amount of the aliphatic monocarboxylic acid may be varied in the range of from 1 to 6 moles per mol of the benzene compound.

The catalytic ingredients, i.e., palladium, arsenic and alkali or alkali earth metal ingredients are usually supported on a carrier. Examples of suitable carriers include silica, alumina, silica-alumina, active carbon, diatomaceous earth, pumice, zeolite, bauxite, magnesia and titania.

The concentration of palladium supported on a carrier may conveniently be in the range of from 0.1 to 10% by weight based on the total weight of the catalyst and the carrier. The amount of arsenic is in the range of from 0.05 to 4 gram atom, preferably from 0.2 to 2 gram atom, per gram atom of the palladium. The amount of an alkali metal and/or an alkali earth metal is in the range of from 0.1 to 10 gram atom, preferably from 2 to 8 gram atom, per gram atom of the palladium.

The catalyst supported on a carrier may be prepared in any convenient manner. For example, a palladium compound and an arsenic compound are dissolved in a suitable solvent. A carrier is impregnated or coated with the so-obtained solution. The solution-impregnated carrier is dried, reduction-treated, impregnated with an aqueous solution of an alkali metal or alkali earth metal compound and finally dried. In another example, only a palladium compound is first dissolved in a solvent. Then, a carrier is impregnated or coated with the palladium compound solution. The solution-impregnated carrier is dried, reduction-treated, and then impregnated with an aqueous solution of an arsenic compound and an alkali or alkali earth metal compound. If desired, the catalyst so prepared may be calcined preferably at a temperature in the range of from 300° to 450° C.

Palladium compounds which can be used for the preparation of the catalyst are, for example, palladium chloride, palladium acetate, palladium nitrate, palladium-sodium chloride and palladium acetylacetonate. Arsenic compounds which can be used include, for example, arsenic acid, diarsenic pentoxide and alkali metal salts of arsenic acid. Alkali and/or alkali earth metal compounds which can be used include, for example, hydroxides of potassium, sodium, lithium, calcium, barium and magnesium; and aliphatic carboxylic acid salts, such as formate, acetate and propionate, of these metals. In the above-mentioned preparation of the catalyst, the reduction treatment of the palladium compound (or plus arsenic compound)-deposited carrier may be carried out by using any convenient reducing agent such as hydrogen, methanol, ethylene, hydrazine and formalin.

The palladium ingredient in the catalyst prepared in the above-mentioned manner is supported in a metallic form on the carrier. The arsenic ingredient in the catalyst is supported in either metallic or oxide form on the carrier. The alkali and/or alkali earth metal ingredient in the catalyst is supported on the carrier in a carboxylate form when the alkali and/or alkali earth metal compound used is a carboxylic acid salt, or in an oxide form when the alkali and/or alkali earth metal compound used is hydroxide. The alkali and/or alkali earth metal ingredient of the latter form, i.e., an oxide form, is presumed to be, during the vapor phase catalytic oxidation reaction of the invention, converted to a carboxylate form because the ingredient reacts with an aliphatic monocarboxylic acid used as a starting raw material.

As a source of molecular oxygen which is used in the process of the invention, pure molecular oxygen, air and a mixture of molecular oxygen and an inert gas such as nitrogen may be used. A relative proportion of molecular oxygen in the gaseous feed mixture to be introduced into a reactor is preferably in the range of from 2 to 40% by volume based on the volume of the gaseous feed mixture.

The catalytic oxidation reaction of the invention is advantageously carried out at a pressure in the range of from atmospheric pressure to ten times thereof. The reaction pressure can, however, be lower or higher than this range. The reaction temperature must be sufficiently high for maintaining the reaction mixture at a gaseous state. Accordingly, the reaction temperature is usually higher than 140° C., preferably in the range of from 180° to 260° C.

The invention is further illustrated by the following example and comparative examples, in which % is expressed by weight unless otherwise specified. In these examples and comparative examples, the catalytic oxidation reaction was carried out by using a tubular glass reactor having an inner diameter of 25 mm and a height of 350 mm.

EXAMPLE 1

0.84 g of palladium chloride was dissolved in 25 ml of aqueous hydrochloric acid, followed by the addition thereto of 24 g of silica pellets each having a size of 3 mm in diameter and 6 mm in height (N608 supplied by Nikki Chemical Co.). The mixture was stirred for approximately five hours. The palladium chloride-supported silica pellets were gradually dried over a period of five hours by using a rotary evaporator and, thereafter, placed in a reducing furnace where the pellets were maintained at 200° C. for two hours and then at 400° C. for two more hours to be reduced in a gaseous stream of methanol-saturated nitrogen. Then, the pellets were impregnated with 20 ml of an aqueous solution having dissolved therein 0.54 g of diarsenic pentoxide and 1.32 g of potassium hydroxide. The solution-impregnated pellets were gradually dried over a period of five hours by using a rotary evaporator.

The catalyst so prepared contained 2% of metallic palladium and had a composition such that the atomic ratio of palladium/arsenic/potassium was 1/1/5.

A gaseous feed comprised of toluene, acetic acid and oxygen was continuously passed through a reactor packed with 10 ml of the above-mentioned catalyst. The feed rates of toluene, acetic acid and oxygen were 81 m mol/hr, 324 m mol/hr and 190 m mol/hr, respectively. The reaction temperature was 230° C. Results are shown in Table I, below.

EXAMPLE 2

In accordance with procedures similar to those mentioned in Example 1, a catalyst was prepared, and the catalytic oxidation reaction was carried out by using the catalyst wherein the feed rates of toluene, acetic acid and oxygen were 60 m mol/hr, 360 m mol/hr and 190 m mol/hr, respectively. All other conditions remained substantially the same. Results are shown in Table I, below.

EXAMPLE 3

In accordance with a catalyst preparation procedure similar to that mentioned in Example 1, a catalyst was prepared wherein 1.08 g of diarsenic pentoxide was used instead of 0.54 g, with all other conditions remaining substantially the same. The catalyst so prepared contained 2% of metallic palladium and had a composition such that the atomic ratio of palladium/arsenic/potassium was 1/2/5.

Using 10 ml of the catalyst, the catalytic oxidation reaction was carried out in a manner similar to that mentioned in Example 1. Results are shown in Table I, below.

EXAMPLE 4

In accordance with a catalytic preparation procedure similar to that mentioned in Example 1, a catalyst was prepared wherein 0.27 g of diarsenic pentoxide was used instead of 0.54 g, with all other conditions remaining substantially the same. The catalyst so prepared contained 2% of metallic palladium and had a composition such that the atomic ratio of palladium/arsenic/potassium was 1/0.5/5.

Using 10 ml of the catalyst, the catalytic oxidation reaction was carried out in a manner similar to that mentioned in Example 1. Results are shown in Table I, below.

COMPARATIVE EXAMPLE 1

In a manner similar to that mentioned in Example 1, palladium chloride was supported on silica pellets, and the silica pellets were treated in a reducing furnace. Then, the silica pellets were impregnated with 20 ml of an aqueous solution having dissolved therein 2.22 g of potassium acetate. The solution-impregnated pellets were gradually dried over a period of five hours by using a rotary evaporator. The catalyst so prepared contained 2% of metallic palladium and had a composition such that the atomic ratio of palladium/potassium was 1:5.

Using 10 ml of the catalyst, the catalytic oxidation reaction was carried out in a manner similar to that mentioned in Example 1. Results are shown in Table I, below.

TABLE I

| Example No. | Catalytic composition (atomic ratio) Pd : As : K | Benzyl acetate obtained | |
|---|---|---|---|
| | | Space time yield* (g/l-cat hr) | Selectivity (%) |
| Example 1 | 1 : 1 : 5 | 150 | 95 |
| Example 2 | 1 : 1 : 5 | 180 | 94 |
| Example 3 | 1 : 2 : 5 | 135 | 98 |
| Example 4 | 1 : 0.5 : 5 | 130 | 98 |
| Comparative Example 1 | 1 : 0 : 5 | 97 | 85 |

*Note
In Examples 1 through 4, the space time yield was reduced only by a negligible extent even when the catalytic oxidative reaction was continued for 1,000 hours. In contrast, in Comparative Example 1, the space time yield was reduced to 58 g/1-cat hr, fifty hours after the commencement of the catalytic oxidation reaction.

EXAMPLE 5

10 ml of a catalyst prepared in a manner similar to that mentioned in Example 1 were packed into a reactor. A gaseous feed comprised of p-xylene, acetic acid and oxygen was continuously passed through the catalyst-packed reactor. The feed rates of p-xylene, acetic acid and oxygen were 60 m mol/hr, 360 m mol/hr and 190 m mol/hr, respectively. The reaction temperature was 230° C.

The space time yields of p-methylbenzyl acetate and p-xylylenediacetate were 64 g/l-cat hr and 9.2 g/l-cat hr, respectively.

EXAMPLE 6

In accordance with a catalyst preparation procedure similar to that mentioned in Example 1, a catalyst was prepared wherein 0.71 g of arsenic acid hydrate ($H_3AsO_4 \cdot \frac{1}{2}H_2O$) and 5.0 g of magnesium acetate were used instead of diarsenic pentoxide and potassium hydroxide, respectively, with all other conditions remaining substantially the same. The catalyst so prepared contained 2% of metallic palladium and had a composition such that the atomic ratio of palladium/arsenic/magnesium was 1:1:5.

Using 10 ml of the catalyst, the catalytic oxidation reaction was carried out in a manner similar to that mentioned in Example 1. The space time yield of and selectivity for benzyl acetate were 138 g/l-cat hr and 95%, respectively.

EXAMPLE 7

In accordance with a catalytic preparation procedure similar to that mentioned in Example 1, a catalyst was prepared with the composition such that the atomic ratio of palladium:arsenic:potassium was 1:0.06:5.

10 ml of the catalyst were packed into a reactor. A gaseous feed comprised of toluene, propionic acid and air was continuously passed through the reactor, wherein the feed rates of each gas were 73 m mol/hr, 292 m mol/hr and 190 m mol/hr, respectively. The reaction temperature was 230° C.

The space time yield and the selectivity of benzyl propionate were 72 g/l-cat hr and 97%, respectively.

COMPARATIVE EXAMPLE 2

1.13 g of palladium chloride and 1.16 g of antimony trichloride were dissolved in 34 g of aqueous hydrochloric acid, followed by the addition thereto of 34 g of silica pellets (N608 supplied by Nikki Chemical Co.). The mixture was stirred for approximately five hours, then dried gradually over a period of five hours by using a rotary evaporator.

The pellets were placed in a reducing furnace and maintained at 200° C. for two hours and then at 400° C. for two more hours to be reduced in a gaseous stream of methanol-saturated nitrogen.

Then, the pellets were impregnated with 20 ml of an aqueous solution containing 3.13 g of potassium acetate. The solution-impregnated pellets were gradually dried over a period of five hours by using a rotary evaporator.

The catalyst so prepared contained 2% of metallic palladium and has a composition such that the atomic ratio of palladium:antimony:potassium was 1:1:5.

A gaseous feed comprised of toluene, acetic acid and air was continuously passed through a reactor packed with 10 ml of the afore-mentioned catalyst. The feed rates of toluene, acetic acid and air were 73 m mol/hr, 321 m mol/hr and 190 m mol/hr; respectively. The reaction temperature was 230° C.

The space time yield and the selectivity of benzyl acetate were 100 g/l-cat hr and 84%, respectively.

What we claim is:

1. A process for preparing an aliphatic carboxylic acid ester of a benzene compound having 1 to 2 hydroxymethyl substituents bound to the nucleus, which comprises the step of contacting, in a vapor phase, a gaseous feed comprised of a benzene compound selected from the group consisting of toluene and o-, m- and p-xylenes, an aliphatic monocarboxylic acid having 2 to 4 carbon atoms and molecular oxygen with a catalyst consisting essentially of (a) palladium, (b) arsenic and (c) at least one metal selected from the group consisting of alkali metals and alkali earth metals, the atomic ratio of palladium:arsenic:the alkali or alkali earth metal being 1:0.05–4:0.1–10, said arsenic ingredient being derived from at least one arsenic compound selected from the group consisting of arsenic acid, diarsenic pentoxide and alkali metal salts of arsenic acid.

2. A process according to claim 1 wherein the atomic ratio of palladium:arsenic:the alkali or alkali earth metal is 1:0.2–2:2–8.

3. A process according to claim 1 or 2 wherein the amount of the aliphatic monocarboxylic acid in the gaseous feed is in the range of from 1 to 6 mols per mol of the benzene compound.

4. A process according to claim 1 or 2 wherein the concentration of the molecular oxygen in the gaseous feed is in the range of from 2 to 40% by volume based on the volume of the gaseous feed.

5. A process according to claim 1 or 2 wherein said contact of the gaseous feed with the catalyst is carried out at a temperature of higher than 140° C.

6. A process according to claim 1 or 2 wherein said contact of the gaseous feed with the catalyst is carried out at a temperature in the range of from 180° to 260° C.

7. A process according to claim 1 or 2 wherein the (a) palladium, (b) arsenic and (c) alkali or alkali earth metal ingredients are supported on a carrier, (a) in metallic form, (b) in metallic or oxide form, and (c) in carboxylate or oxide form, respectively.

8. A process according to claim 7 wherein the concentration of palladium supported on a carrier is in the range of from 0.1 to 10% by weight based on the total weight of the catalyst and the carrier.

9. A process according to claim 7 wherein said catalyst is prepared by the steps of:
   dissolving a palladium compound and an arsenic compound in a solvent;
   impregnating or, coating a carrier with the so-obtained solution, followed by drying;
   subjecting the palladium and arsenic compounds-deposited carrier to a reduction treatment, and;
   impregnating the reduction-treated carrier with a solution of the alkali or alkali earth metal compound, followed by drying.

10. A process according to claim 7 wherein said catalyst is prepared by the steps of:
    dissolving a palladium compound in a solvent;
    impregnating or coating a carrier with the palladium solution, followed by drying;
    subjecting the palladium compound-deposited carrier to a reduction treatment, and;
    impregnating the reduction-treated carrier with a solution of an arsenic compound and the alkali or alkali earth metal compound, followed by drying.

* * * * *